(12) United States Patent
Kelly et al.

(10) Patent No.: US 8,999,012 B2
(45) Date of Patent: Apr. 7, 2015

(54) QUALITY CERTIFICATION OF OXYGENATED GASOLINE

(75) Inventors: Francis X. Kelly, Alexandria, VA (US); Tian Chong Lau, Ontario (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 320 days.

(21) Appl. No.: 13/101,580

(22) Filed: May 5, 2011

(65) Prior Publication Data
US 2012/0279114 A1 Nov. 8, 2012

(51) Int. Cl.
*C10L 1/182* (2006.01)
*G01N 33/22* (2006.01)
*C10L 1/02* (2006.01)
*G05D 21/02* (2006.01)

(52) U.S. Cl.
CPC .............. *C10L 1/023* (2013.01); *G01N 33/22* (2013.01); *G05D 21/02* (2013.01)

(58) Field of Classification Search
CPC ............ C10L 1/023; C10L 1/04; C10L 1/06; G05D 21/02
USPC ................................ 703/2; 44/451; 73/64.56
See application file for complete search history.

(56) References Cited

U.S. PATENT DOCUMENTS

| 5,600,134 A | 2/1997 | Ashe et al. |
| 6,258,987 B1 | 7/2001 | Schmidt et al. |
| 2009/0158824 A1 | 6/2009 | Brown et al. |
| 2009/0292512 A1 | 11/2009 | Wolf |
| 2010/0131247 A1* | 5/2010 | Carpenter et al. ................. 703/2 |
| 2011/0249261 A1* | 10/2011 | Mertens ......................... 356/326 |

OTHER PUBLICATIONS

PCT International Search Report issued Jun. 25, 2012 in corresponding PCT Application No. PCT/US2012/036277, 3 pgs.
PCT Written Opinion issued Jun. 6, 2012 in corresponding PCT Application No. PCT/US2012/036277, 5 pgs.

* cited by examiner

*Primary Examiner* — James Goloboy
*Assistant Examiner* — Latosha Hines
(74) *Attorney, Agent, or Firm* — Malcolm D. Keen; Glenn T. Barrett; Andrew T. Ward

(57) ABSTRACT

A method for controlling the manufacture and certification of an oxygenated gasoline product is carried out by manufacturing a gasoline Basestock for Oxygenate Blending (BOB) at a refinery site in accordance with an empirical relationship, valid for at that site under typical manufacturing conditions, between (i) a property value of the BOB stream such as octane as determined by an on-site online process analyzer and (ii) the corresponding instantaneous value or FPAPV property value as determined by the test method mandated by the product specification for the final gasoline stream when blended with the required proportion of oxygenate. The quality of fit of this empirical relationship is calculated according to the standard deviation of the residuals of the relationship and a confidence level is fixed so that the final oxygenated gasoline formulated with the BOB will meet the required property specification when measured by the test method mandated by the specification. The final oxygenated gasoline blend is certified as having a property value conforming to the required specification based on the predicted property value for the finished gasoline.

8 Claims, 1 Drawing Sheet

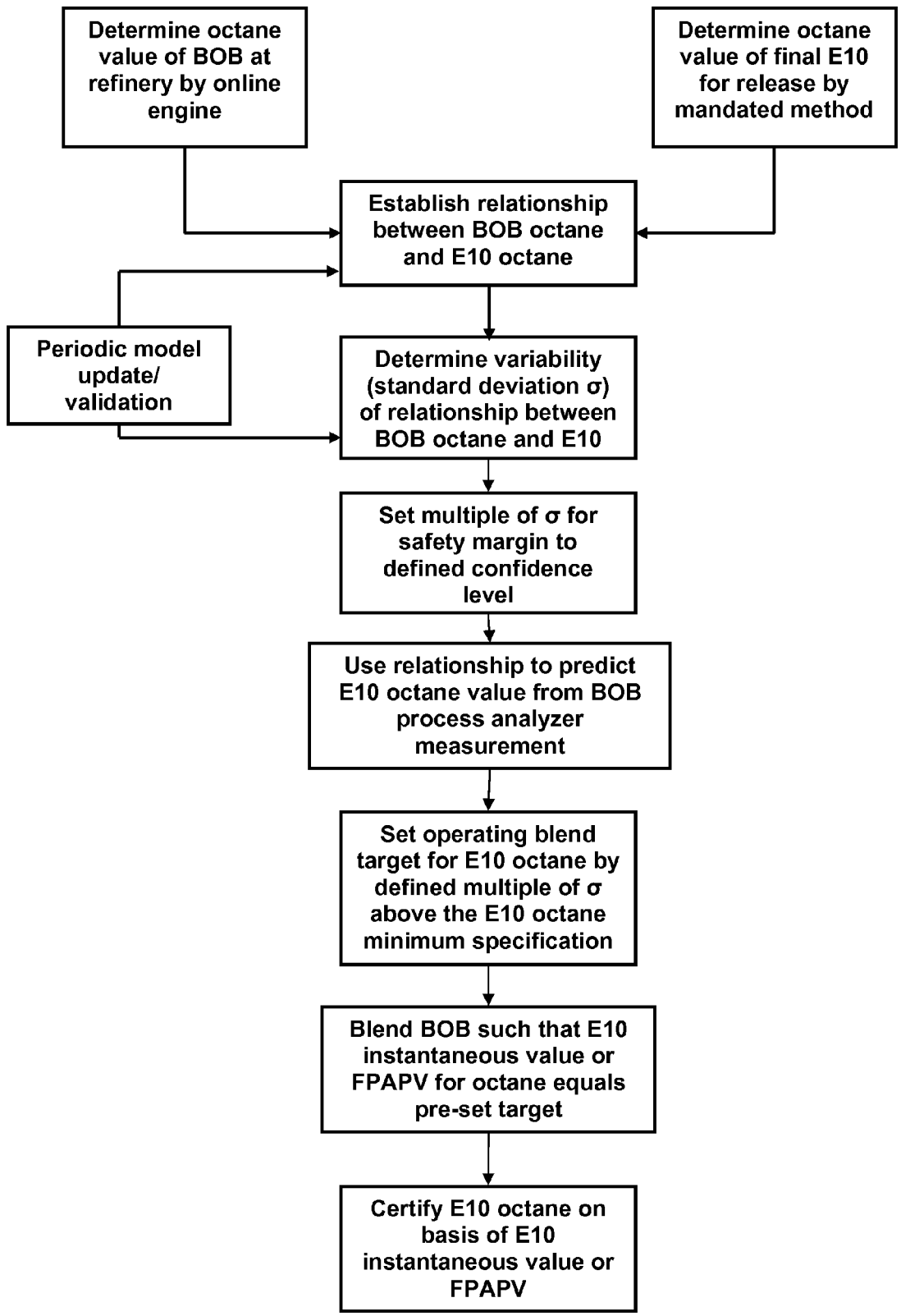

QUALITY CERTIFICATION OF OXYGENATED GASOLINE

The present invention relates to a method for manufacturing oxygenated gasoline and for certifying the quality of the blended gasoline product.

BACKGROUND OF THE INVENTION

Conventional (ethanol-free) mogas (gasoline sold at the pump for road use) has been largely replaced by ethanol-containing gasoline in the United States; other countries are also mandating the use of oxygenates such as ethanol in gasoline. As ethanol is typically blended at the distribution terminal (and not at the refinery gasoline blend header), problems arise in the operation of the overall manufacturing and distribution process. Ethanol-free gasoline is typically produced within a refinery as a finished product which fully meets all necessary specifications for sale as an ethanol-free product. This finished gasoline can be manufactured to fit the required product specifications very precisely because analytical data for the product can be obtained during the manufacture (aka gasoline blending) process and used to control the blending process. As a consequence, manufacturing costs are kept to a minimum because expensive blendstocks are usually not wasted by exceeding specifications. Unfortunately, this type of precise manufacturing control is not possible for blending configurations where the final commercial grade ethanol-containing gasolines are prepared by mixing a non-ethanol containing subgrade blend manufactured at a refinery with ethanol at a location remote from the refinery.

As explained in U.S. Pat. No. 6,258,987 (Schmidt), the ethanol is not usually blended into the finished gasoline within the refinery because the ethanol is water soluble. As a consequence of this solubility, an ethanol-containing gasoline can undergo undesirable change if it comes in contact with water during transport through a distribution system, which may include pipelines, stationary storage tanks, rail cars, tank trucks, barges, ships and the like: absorbed or dissolved water will then be present as an undesirable contaminant in the gasoline. Alternatively, water can extract ethanol from the gasoline, thereby changing the chemical composition of the gasoline and negatively affecting the specification of the gasoline, possibly leading to regulatory violations since the government may require a certain oxygenate content in the gasoline sold at the pump. Government regulation in the U.S., for example, has until recently limited the oxygen content of gasoline to 4.0 wt. % while also requiring that reformulated gasolines contain at least 1.5 wt. % of oxygen, resulting in the gasoline known as E10 when ethanol is used as the oxygenate at nominally 10 vol %. More recent regulations propose a grade known as E15 for newer vehicles and other grades are also on sale, for example, E85, for use in multi-fuel engines.

In order to avoid contact with water as much as possible, ethanol-containing gasoline is usually manufactured by a multi-step process in which the ethanol is incorporated into the product at a point which is near the end of the distribution system, e.g. at the product distribution terminal, "at the rack". More specifically, gasoline which contains a water soluble oxygenate such as ethanol, is generally manufactured by producing an unfinished and substantially hydrocarbon precursor subgrade or blendstock usually known as a Blendstock for Oxygenate Blending (BOB) at the refinery, transporting the BOB to a product terminal in the geographic area where the finished gasoline is to be distributed, and mixing the BOB with the desired amount of alcohol at the terminal.

When a BOB is manufactured at the refinery, the properties of the BOB are measured and controlled to intermediate specifications that differ from the finished E10 gasoline in order to compensate for the effects of oxygenate which will be added after the BOB leaves the refinery. The effects of oxygenates such as ethanol and methanol are variable and can depend on the chemical composition of the BOB. For example, the addition of ethanol has a substantial effect on gasoline volatility as well as the distillation curve, and the magnitude of this effect is dependent on the chemical composition of the BOB. In addition, blending ethanol into gasoline results in a non-ideal solution that does not necessarily follow linear blending relationships.

The variable effects which result when an oxygenate such as ethanol, is mixed with a subgrade blend (BOB) to form a finished gasoline are taken into account by setting BOB manufacturing specifications that are different than the finished E10 gasoline commercial specifications to account for the Ethanol effect. These BOB specifications include a margin for error to accommodate the variable effect of the oxygenate, e.g. ethanol. In addition to the variability of the effect of the oxygenate on the intrinsic property value of the finished gasoline, additional variability can be introduced into the measured results of the finished gasoline property due to the effect of the oxygenate on the intrinsic variability of the analytical test method, and sample handling related to addition of the oxygenate in the laboratory. Because failure to adequately allow for the margin for error can lead to violation of the required commercial specifications for the finished gasoline, this can add cost to the manufacturing process since more expensive blendstocks may be required to achieve the necessary margin for error.

Various proposals have been published for avoiding the need for blending the subgrade to excessively stringent specification in order to ensure regulatory compliance when the oxygenate is added at a distant location. U.S. Pat. No. 6,258,987, mentioned above, for example, proposes a process which involves withdrawing a sample of the subgrade, mixing it with a known amount of alcohol, analyzing properties of the mixture, and using the analysis results to control and optimize the blending process.

US 2009/0292512 (Wolf), while not dealing directly with the manufacturing offset issue, does recognize that the vapor pressure of oxygenated fuels, particularly alcohols such as ethanol, propanol and butanols, and esters, ketones, etc., are non-ideal, and complicate the blend models for such oxygenated fuels and proposes a method for predicting the distillation characteristics of oxygenated blends.

US 2009/0158824 (Brown) proposes a method for analyzing gasoline or diesel fuel products and certifying their quality for regulatory purposes. In this method, a representative sample of a manufactured petroleum refinery product is analyzed and certified upon completion of product manufacture using the on-line process analyzer(s) used to monitor the manufacture of the product. The representative sample is re-introduced into the on-line process analyzer(s) for analysis, with the on-line process analyzer(s) operating strictly as a product certification analytical system. By using the same process analyzers to both monitor and also certify manufactured petroleum product, manufacture offset from specification can be reduced and the reduction in manufacturing offset directly reduces the cost of the blended or manufactured product while maintaining the same risk of non-conformance. While not addressing the problem of oxygenate blending directly, this technique would find application in certifying oxygenate-containing gasoline blends with greater certainty and reduced manufacturing costs if the reintroduced sample were to include oxygenate in the prescribed percentage proportion.

A recently published proposal in US 2010/0131247 (Carpenter) for controlling the composition of the subgrade which will yield an oxygenate-containing gasoline meeting specification when mixed with the desired amount of oxygenate involves modeling the BOB subgrade using spectroscopic measurements and associating the subgrade characteristics in the model to the properties of the finished oxygenate-containing gasoline. In this way, a laboratory analysis for the oxygenate-containing gasoline properties can be predicted and used to control and optimize the blending process for the subgrade. The use of chemometric models to predict the oxygenate-containing finished gasoline properties from spectroscopic data for the subgrade BOB enables on-line spectroscopic analysis of a product stream to make necessary adjustments to blend the components of the BOB to maintain oxygenate-containing finished gasoline properties based on model predictions.

While the use of chemometric models as described in US 2010/0131247 represents one way to assure compliance of the finished gasoline with specification, the development of the required, highly detailed models is itself time-consuming and possibly subject to error arising from misinterpretation and correlation between the properties of the finished gasoline and those of the BOB subgrade.

SUMMARY OF THE INVENTION

We have now devised a method for controlling the manufacture of the BOB subgrade which enables the quality of the finished, oxygenate-blended gasoline formulated from the subgrade to be certified without the necessity of generating complicated models relating spectral properties to product specifications. As such, the method is simple and reliable. It uses online process analyzers to measure and control the properties of the oxygenate-free stream (BOB) in accordance with the predicted effect of the oxygenate component in the finished gasoline so as to permit certification of the finished gasoline product with adequate assurance of compliance.

According to the present invention, a gasoline Basestock for Oxygenate Blending (BOB) is manufactured at a refinery site in accordance with an empirical relationship, valid for that refinery site under typical manufacturing conditions, between (i) a property value of the BOB stream, e.g. octane as determined by an on-site online process analyzer, and (ii) the corresponding property value for the final gasoline stream when blended with the required proportion of oxygenate and measured by the specification mandated test method. The quality of fit of this empirical relationship is calculated according to the standard deviation of the residuals of the relationship. The final oxygenated gasoline blend may then be certified as having a property value conforming to the specification property value on the basis of the predicted property calculated using the established relationship and the BOB property value as measured at the refinery.

The manufacturing and certification is carried out by the following steps:

(a) establishing a relationship for a single manufacturing site to be used for the manufacture of an unoxygenated gasoline subgrade Base for Oxygenate Blending (BOB) stream under defined refining conditions used at that site, between (i) a property value of the BOB stream as determined by an on-site online process analyzer and (ii) the corresponding property value of the BOB stream when blended with the proportion of oxygenate required by the final oxygenated blend specification and when measured by the test method mandated by the product specification;

(b) establishing the quality of fit of the established relationship as characterized by the standard deviation of the residuals of the relationship (the differences between the measured and predicted property values of the finished gasoline);

(c) setting a manufacturing target for the finished (e.g. E10) gasoline property value using a predicted property value for the finished oxygenated (e.g. E10) gasoline based on the previously established relationship and the property value of the BOB measured by the online process analyzer and controlling the blend to this target using either the current predicted Flow Proportioned Average Property Value (FPAPV) or predicted instantaneous value of the property of the finished oxygenated gasoline to produce the BOB subgrade.

The manufacturing target value for the property of the finished (e.g. E10) gasoline is generally set as a calculated function of (1) the property specification for the finished oxygenated gasoline, (2) the quality of fit of the established relationship as characterized by the standard deviation of the residuals, and (3) a confidence level that the final oxygenated gasoline formulated with the manufactured BOB will meet the property specification when measured by a primary test method.

Following manufacture of the BOB subgrade at the refinery, it may then be transported to a gasoline distribution terminal and blended there with the specification proportion of oxygenate to form the final oxygenated gasoline blend.

The final oxygenated gasoline blend may be certified as meeting the specification requirement on the basis of the predicted instantaneous value or FPAPV of the oxygenated gasoline blend. Certification may be made on the basis of the instantaneous value when simultaneously blending the BOB and releasing it without transferring to tankage; when the BOB is released on a batch basis, certification is required to be done upon the FPAPV values. The instantaneous values may also be used when setting the manufacturing target without the need for certification.

The present method is applicable to the manufacture and certification of gasoline properties including, but not restricted to, octane (research octane, motor octane, road octane), vapor pressure, Reid Vapor Pressure, distillation characteristics such as T10, T50 and T90, and the vapor/liquid ratio at 20° C. (T V/L=20) which are subject to variation on the addition of the oxygenate to the initial BOB subgrade which leaves the refinery.

The property of the final oxygenated gasoline which is to be certified can be related to either the corresponding property measured on the BOB (e.g. computing the E10 RVP from the BOB RVP) or to a related property which can be derived directly from other BOB properties, for example, by relating the E10 T50 to BOB distillation points different than the T50 point.

Oxygenates which come within the class of possible blending components include ethanol, propanol, t-butanol, ethers (when legally permitted), such as methyl t-butyl ether, ethyl t-butyl ether and methyl t-amyl ether, ketones such as methyl ethyl ketone, although ethanol is likely to be the one most commonly used in view of its current availability, especially from bio-sources and for this reason, the present invention is described in detail below, for convenience and brevity, with reference to ethanol in an E10 blend although it is applicable to use with other oxygenate blendstocks, with other blend components which may be added to the refinery blendstock and other final product specifications, e.g. E15.

THE DRAWINGS

The single FIGURE of the accompanying drawing is a simplified flowsheet of the method steps used for product manufacture and certification according to the present invention.

DETAILED DESCRIPTION

For gasoline blendstocks intended to be blended with an oxygenate such as ethanol, certification is generally done by testing samples blended with ethanol in the laboratory, since (a) the quality specifications are set with reference to the fuel after blending with ethanol, and (b) unlike other gasoline blend components, ethanol is typically blended at the terminal and not at the refinery gasoline blend header (where the samples sent to the process analyzers are drawn). In this case, multiple additional uncertainties may be introduced to the determination of the property value of the ethanol-containing gasoline: (a) the effect of ethanol addition on the intrinsic property (e.g. octane) value, (b) the laboratory test variability, (c) the effect of the presence of ethanol on the test variability, (d) the effect of additional sample handling required to blend the ethanol with the BOB in the laboratory and (e) variability in the laboratory ethanol addition rate. When combined, these uncertainties necessitate an higher average product quality giveaway for laboratory-certified ethanol-containing gasoline than seen with online/FPAPV certified conventional gasoline which contains no ethanol. Specifically, to minimize probability of an off-specification laboratory test on the ethanol-gasoline blend, a suitable statistically-based buffer is established between the operating target and the gasoline specification.

This invention enables the product quality giveaway for ethanol-containing gasoline to be reduced by enabling online control and online certification of the ethanol-containing gasoline properties to be made using either the instantaneous value or the FPAPV (Flow Proportioned Average Property Value (defined in ASTM D6624-06) of the finished oxygenated gasoline formulated with the ethanol-free BOB blendstock passing through the refinery blend header. The instantaneous value or FPAPV is calculated by converting the process analyzer measurement of a BOB property to a corresponding property of the finished ethanol-containing gasoline, via application of the established relationship between the BOB and the finished gasoline properties. In the case of octane, this relationship may typically be a simple linear relationship of the form:

$$RON_E 10 = a*RON_{BOB} + b$$

where a and b are empirically determined coefficients. Alternatively, the relationship may include additional terms as appropriate to reduce the standard deviation of the residuals of the relationship.

The property value or values typically determined by the online process analyzers are used in conjunction with the established relationships to control the blend recipes to meet the predicted E10 target during the BOB blending operation. The final oxygenated product, e.g. E10, is then certified based on the instantaneous value or FPAPV of the predicted E10 property calculated from the analyzer results and the associated flow through the blend header. Typically, the online blend control system is capable of producing blends with properties (e.g. as calculated via FPAPV) very close to the control target.

The FIGURE shows a simplified flow schematic of the basic steps of the present method, as applied to the determination of the octane value of the gasoline; other properties such as the distillation characteristics which are also affected by the addition of ethanol may also be predicted and certified in the same manner. The sequence of operations described below and shown in the FIGURE is for the octane of a refinery BOB and a final E10 gasoline but the same or similar sequence would be appropriate for different properties, e.g. distillation, different refinery blendstocks and different oxygenates added at a location distant from the refinery.

First, the octane value of the refinery subgrade BOB and of the final E10 gasoline with the added ethanol are determined in the steps identified as "Determine octane value of BOB at refinery by online engine" and "Determine octane value of final E10 for release by mandated method". As designated, the refinery will use an online octane analyzer such as a test engine while the determination of the E10 octane will be made by the test method mandated by the specification such as ASTM D2699/D2700, since the initial objective is to relate the octane of the BOB subgrade as measured by the online octane engine to the E10 octane as measured by a mandated test method, that is, an approved regulatory test method or a contractually required test method. This comparison is extended over a period of time and a sufficient number of samples of the BOB and the E10 to determine the mathematical relationship between the BOB and E10 octane determinations and the variability of the mathematical relationship. This step is identified as "Establish relationship between BOB octane and E10 octane" More generally, this step entails the establishment of a relationship between the property values of the BOB stream determined by the on-site online process analyzer and related, derivable property values of the final oxygenated gasoline. The next step, identified as "Determine variability (standard deviation) of relationship between BOB octane and E10 octane" entails the statistical calculation of the time/sample variation as the standard deviation a between the measured and predicted (via the established relationship) values of the E10 octane.

A safety margin is then superimposed upon the finished gasoline specification to provide an adequate level of confidence for the certification of the product: "Set multiple of a for safety margin to defined confidence level". The safety margin is calculated based upon this standard deviation in such a way as to ensure a prescribed confidence level (e.g. 95%) that the final E10 product is on-specification when determined by the corresponding primary test method i.e. the mandated test method, after the BOB has been blended with ethanol at the distant terminal and when the inferred E10 property value measured at the refinery is at the safety margin.

The next step, identified as "Use relationship to predict E10 octane value from BOB process analyzer measurement", enables the calculation of an instantaneous or FPAPV of the E10 octane by which the blend recipe can be controlled.

The operating target at the refinery is then set according to the desired octane value for the E10 product, taking into account the prescribed safety margin: "Set operating blend target for E10 octane by a defined multiple of G above the E10 minimum specification". The BOB subgrade is then blended to the defined E10 operating target for octane and released from the refinery: "Blend BOB such that E10 instantaneous value or FPAPV for octane equals pre-set target". Consistent with the expectation of blending with the ethanol at the product terminal, certification is made on the basis of the calculated E10 octane value (instantaneous or FPAPV).

When product certification is to be carried out on the basis of the present method, the following steps "Periodic model update/validation" are taken to ensure that the method is adequate to certify product for release:
1. The initial correlation relationship between the BOB property value and the oxygenated gasoline property is established and used as the basis of the model for predicting the finished gasoline property.
2. An operating envelope is established within which the oxygenated gasoline instantaneous value or FPAPV method can be used for certification, and outside which, laboratory certification is required.
3. A quality assurance protocol is developed to monitor the method to ensure the method remains fit-for-use; generally this will imply validation of the procedure on a regular basis, for example, by validation of the results from the model with the regulatory laboratory method. The validity of the operating window within which the method is valid is also to be confirmed by regular validation of the correlation results with the laboratory method using the final, oxygenated blend, for example, with every five refinery blend batches (blend batches, e.g. of about 50,000 barrels).

One possible validation method is to apply Western Electric rules (the decision rules used in statistical process control, for detecting non-random conditions on control charts) to this periodic validation check on the difference between the mandated method on the final oxygenated blend and the value predicted by the model. Satisfying the control chart rules can be interpreted as an indication that the model remains fit for use. Violations of these control chart rules typically include: (a) a single observation (of the difference) being larger than three times the standard deviation of the established relationship between the BOB and finished gasoline property; (b) two of three consecutive observations being larger than two times the standard deviation and having the same algebraic sign; (c) four of five consecutive observations being larger than one standard deviation and having the same sign; and (d) nine consecutive observations with the same sign. Alternatively, validation of the method can be done using control charting techniques as set out in ASTM D6299.

Available in the *Statistical Quality Control Handbook*. (1 ed.), Indianapolis, Ind.: Western Electric Co., OCLC 33858387, © Western Electric Company (1956).

The present method is based upon an empirical, historical model developed for a single refining site using the typical refining conditions at that site to determine the operating envelope within which the model may be used for product certification. Generally, the model will be grade specific, that is, specific to regular grade (87(R+M)/2), mid-grade (88-90) and premium (91+) and will also be seasonally split between summer and winter grades according to regulatory requirements. Other variations in the model may be introduced as desired although with consequent complication. The empirical model has been found to be valid and reliable under these circumstances and is easier to implement than many chemometric models.

The method utilizes this empirical correlation between the property value, e.g. octane of the subgrade BOB (ethanol-free) and the property as realized in the final oxygenated gasoline, e.g. E10, as determined by a mandated specification test method; this may be the manufacturer's own laboratory testing of samples (either taken from the terminal after oxygenate blending, or with the oxygenate blended into a BOB sample in the laboratory) or third party testing of such samples using an approved test method such as ASTM D2699/D2700 for E10 octane ratings. Generally the relationship will be found to be linear and will be valid with the defined operating envelope for the defined grade. This relationship is used to establish the buffer or offset away from the final product specification so that an operating blend target can be established for the with-oxygenate instantaneous value or FPAPV measurement of the refinery subgrade BOB which will be used for blending at the terminal to formulate the final, certified oxygenated product.

Initially the variability of the correlation between the refinery BOB property and the final product property is statistically determined from the residuals between the two sets of property values (between the measured finished gasoline property and the predicted finished gasoline property). This calculation determines the quality of the fit between the finished gasoline (e.g. E10) instantaneous value or FPAPV and the corresponding property of the finished gasoline as measured by the test method mandated by the specification, and acts as a validation of the correlation model since an excessive standard deviation implies that the variations in the model are too great for it to be relied on as a basis for certification. The quality of fit is determined by the magnitude of the standard deviation and will typically be regarded as adequate for the present correlative method if it is less than a factor of two times the published reproducibility of the test method mandated by the specification and preferably less than one times the published reproducibility. Ideally, the quality of fit should be less than 0.75 times the published reproducibility of the test method mandated by the specification.

The historical and ongoing analysis of the correlation enables the standard deviation of the long-term variability between the correlated E10 property of the subgrade and the E10 property measured by a primary test method to be calculated. Given that this correlation is both historical and empirical, the present method should be used only when the refinery is operating within a pre-defined operating window or envelope such that the correlation between the BOB property value and the final gasoline property value remains valid; for this reason, the method is typically to be used on a grade-specific, seasonalized basis with periodic validation of the statistical model.

The safety margin superimposed on the finished gasoline specification is set to provide the level of confidence appropriate to the final use of the E10 value and consistent with conventional certification practices (i.e. laboratory test on finished gasoline with the mandated method); under the standards of these practices, the degree of confidence may properly be less than complete since testing variability may itself introduce discrepancies when retested by the primary test method. If certification is to be made on the basis of the blended E10 product using a primary test method, the level of confidence need be only as stringent as needed to assure satisfactory manufacture although running the risk of occasional re-blending operations if the primary test method discloses an off-specification product. When the instantaneous value or FPAPV calculated value for the finished gasoline is however to be used for product certification, a more demanding standard may be required; this may be at the expense of a minor octane (or other property) give-away but this will be less than with conventional methods.

Typically, when product certification is performed with the mandated test method after addition of oxygenate in the laboratory, the refinery blend target will be set as a multiple of the standard deviation of the long-term variability between the property values of the final product and the BOB subgrade property values measured at the refinery (essentially the manufacturing+testing variability). The multiple is a function of the refinery's capability to reblend product batches which test off-specification in the primary test laboratory. This multiple is typically set at no more than 3 standard deviations from the required product specification and if a refinery can easily and economically reblend product batches, it may be set at 2 or even lower, e.g. 1.5, standard deviations. The quality of the fit between the refinery BOB property measurement and the E10 property value is dependent on several factors including the actual preparation of the E10, the testing of the E10 by the primary test method and also, significantly, by the interaction between batches of different composition and the effect of the ethanol. The refinery blend target should take into account all these factors and include them when setting the blend target for the BOB.

Whether the instantaneous or FPAPV-calculated finished gasoline property is used for product certification or simply for blending control, the refinery manufacturing (blend) target is set so that the calculated finished gasoline property matches the established target value. If necessary, the blend formula for the BOB is adjusted during the blend to achieve the proper FPAPV for the grade in question, for example, by varying the relative amounts of alkylate, reformate, FCC gasoline, straight run naphtha in the blend.

The invention claimed is:

1. A method to control the manufacture of an oxygenated gasoline stream by:
   (a) establishing a relationship for a single manufacturing site used for the manufacture of an unoxygenated gasoline subgrade Basestock for Oxygenate Blending (BOB) stream under defined refining conditions used at that site, between (i) the octane number of the BOB stream as determined by an octane engine that is operationally connected to the output of a gasoline blender at the single manufacturing site and (ii) the octane number of the BOB stream when blended with the proportion of oxygenate required by a final oxygenated blend specification;
   (b) establishing the quality of fit of the established relationship as characterized by the standard deviation of the residuals of the established relationship;
   (c) establishing a manufacturing target value for the octane number of the finished oxygenated gasoline in accordance with the established relationship such that the final oxygenated gasoline formulated with the manufactured BOB will meet the octane number specification when measured by a test method mandated by the specification at a pre-defined confidence level, and
   (d) blending the BOB using a process analyzer that is operationally connected to the output of a gasoline blender at the single manufacturing site such that the blend recipe is controlled to meet a calculated instantaneous value or FPAPV for the final oxygenated gasoline octane number matching the established target, based on the relationship established between the BOB and the finished oxygenated gasoline octane number.

2. A method according to claim 1 which includes:
   (e) transporting the manufactured BOB to a gasoline distribution terminal;
   (f) blending the BOB with the specification proportion of oxygenate at the terminal to form the final oxygenated gasoline blend.

3. A method according to claim 1 in which the manufacturing target value for the octane number of the finished oxygenated gasoline is set to include a confidence level of no less than 95% confidence.

4. A method according to claim 1 which includes the step of certifying the final oxygenated gasoline blend as having an instantaneous value or FPAPV property value on the basis of the octane number of the BOB stream and the established relationship.

5. A method according to claim 1 in which the relationship between the octane number of the BOB stream and the related, derivable octane number of the BOB stream when blended with the proportion of oxygenate required by the final oxygenated blend specification is linear.

6. A method according to claim 1 in which the oxygenate is ethanol.

7. A method according to claim 1 in which the final oxygenated gasoline is nominally 10 vol % ethanol (E10).

8. A method according to claim 1 in which the manufacturing target value is set at no more than 2 standard deviations of the long-term variability between the octane number of the final oxygenated gasoline and the BOB octane number measured by the octane engine that is operationally connected to the output of a gasoline blender at the single manufacturing site.

* * * * *